US00PP32049P2

(12) United States Plant Patent
McGowan

(10) Patent No.: US PP32,049 P2
(45) Date of Patent: Aug. 11, 2020

(54) ***FOTHERGILLA* PLANT NAMED 'ALICE'**

(50) Latin Name: *Fothergilla intermedia*
Varietal Denomination: ALICE

(71) Applicant: Bernard J McGowan, Egremont, MA (US)

(72) Inventor: Bernard J McGowan, Egremont, MA (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,066

(22) Filed: Feb. 14, 2019

(51) Int. Cl.
*A01H 5/12* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct cultivar of *Fothergilla* plant named 'ALICE' is disclosed, characterized by colorful Summer and Fall foliage, and easy rooting. Its compact size is well suited to container production. The new variety is a *Fothergilla*, normally produced as an outdoor garden or container plant.

4 Drawing Sheets

Latin name of the genus and species: *Fothergilla intermedia.*

Variety denomination: 'ALICE'.

BACKGROUND OF THE INVENTION

The new *Fothergilla* cultivar is a product of a planned breeding program conducted by the inventor, Bernard McGowan, in Montague, Mass. The objective of the breeding program was to produce new *Fothergilla* varieties with heightened Fall color on a compact, strong-growing plant. The open pollination resulting in this new variety was made during June of 2001.

The seed parent is an unnamed, unpatented variety of *Fothergilla intermedia*. The pollen parent is unidentified, as this was an open pollination program. The new variety was selected by the inventor in a group of seedlings resulting from the 2001 crossing, in a nursery in Montague, Mass., in May 2004.

Asexual reproduction of the new cultivar was performed by softwood terminal cuttings. This was first performed at a nursery in Montague, Mass. in 2004 and has shown that the unique features of this cultivar are stable and reproduced true to type in 14 successive generations. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'ALICE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALICE' These characteristics in combination distinguish 'ALICE' as a new and distinct *Fothergilla* cultivar:

1. Easy to root.
2. Colorful Summer and Fall foliage.
3. Compact size well suited to container production.

Plants of the new cultivar 'ALICE' are similar to plants of the seed parent in most horticultural characteristics, however, plants of the new cultivar 'ALICE' differ in the following;

1. The new variety has brighter, more vibrant Fall color than the seed parent.

COMMERCIAL COMPARISON

Plants of the new cultivar 'ALICE' are comparable to the unpatented, commercial variety *Fothergilla* 'Mount Airy'. The two *Fothergilla* varieties are similar in most horticultural characteristics; however, the new variety 'ALICE' differs in the following:

1. The new variety has darker red Fall foliage than this comparator.
2. The new variety has is a more compact plant than this comparator.

BRIEF DESCRIPTION OF THE PHOTOGRAPHS

The accompanying photograph in FIG. 1 illustrates in full color a typical plant of 'ALICE' grown in the ground during early Spring in Grand Haven, Mich.

Figure 1:
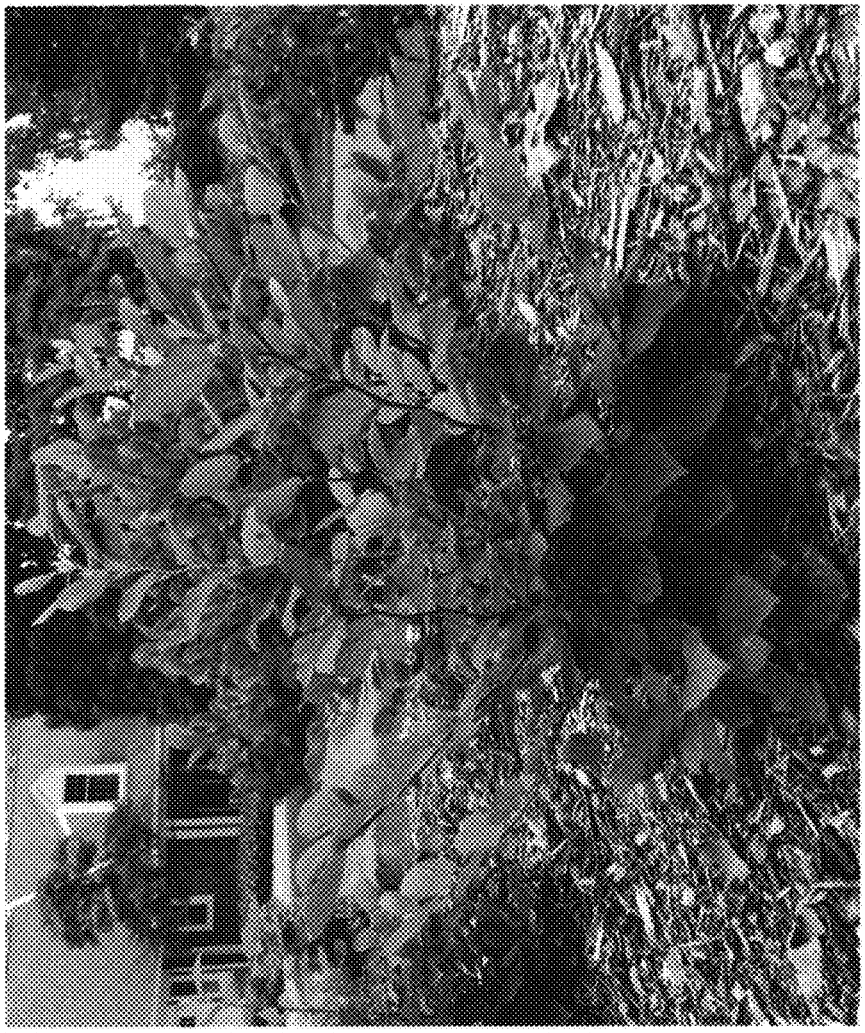
Figure 2:
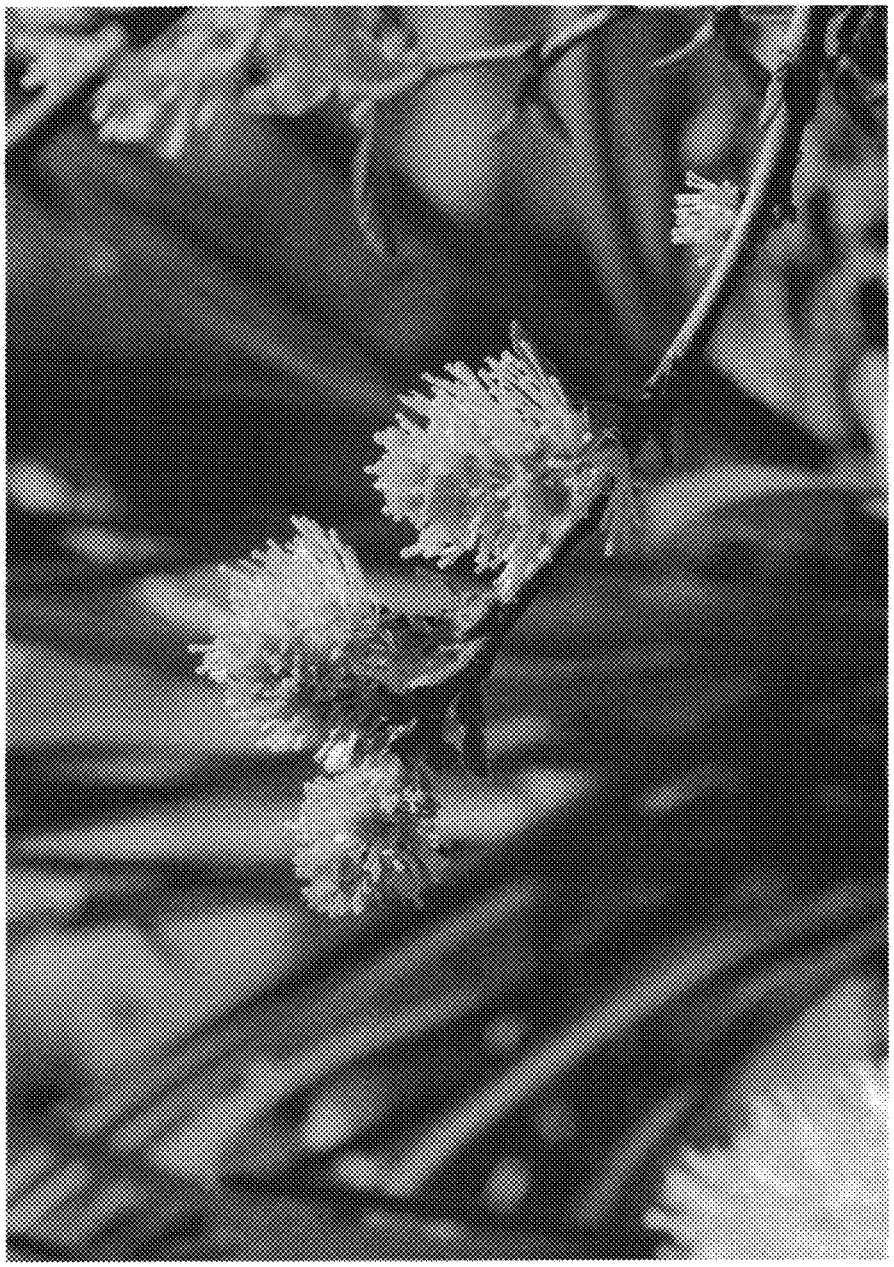
FIG. 2 illustrates a close up view of the flowers.
Figure 3:
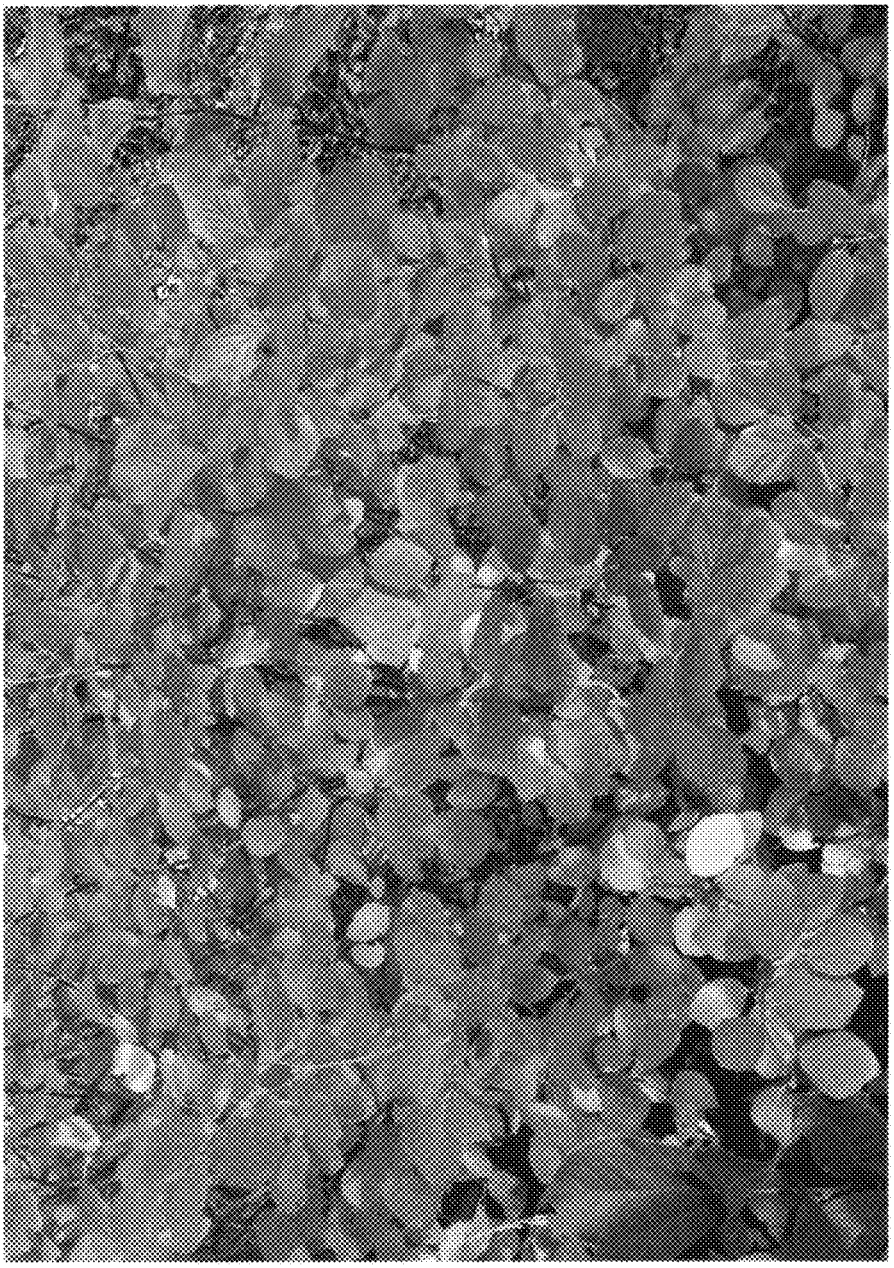
FIG. 3 illustrates foliage color during the last week of August in Grand Haven, Mich.
Figure 4:
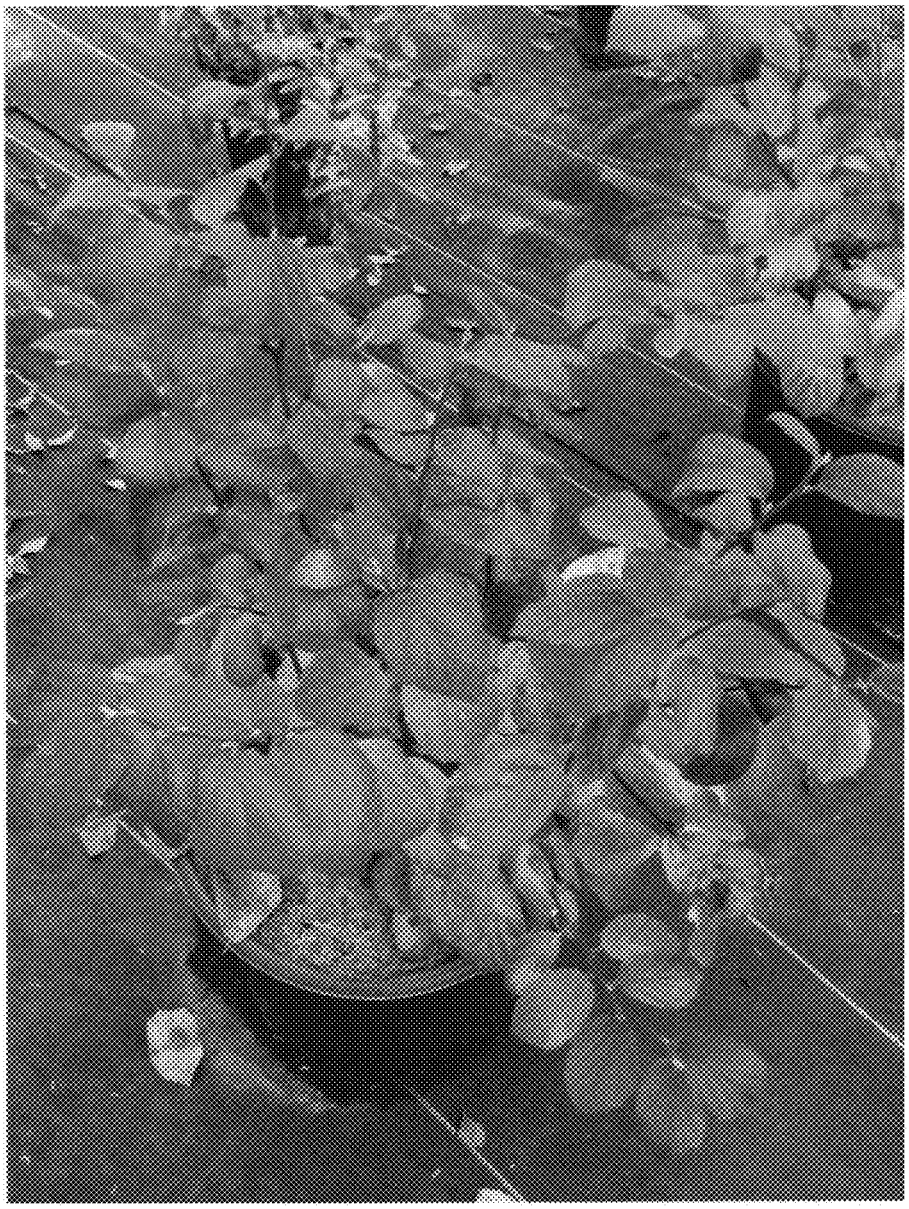
FIG. 4 illustrates Fall foliage color during mid-November in Grand Haven, Mich. Age of the plant photographed is approximately 2 years old from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'ALICE' plants grown in a double poly greenhouse, in Grand Haven, Mich. The growing temperature averaged from 18-27° C. during the day and from 5-10° C. during the night. The double poly was present from Fall through Winter, then removed in the Spring. Shade cloth was used through the Summer. Measurements and numerical values represent averages of typical plant types.

Botanical classification: *Fothergilla intermedia* 'ALICE'.

PROPAGATION

Type of propagation typically used: Softwood cuttings.

Time to initiate roots: 5 weeks at 18-27° C.

Number of days to produce a rooted liner in summer: 3 months at 18-27° C.

Root description: Thin to thick, fibrous, moderate density, and moderate branching. Tan to white in color, not accurately measured by R.H.S. chart.

PLANT

Type of plant: Perennial deciduous flowering shrub.

Age of plant described: 2 to 3 years old.

Container size of the plant described: 3 gallon pot.

Growth habit: Upright and outwards.

Height: 28 cm.

Plant spread: 39 cm.

Plant vigor: Moderate.

Branching characteristics: Upright and outwards.

Characteristics of primary lateral branches:

- *Length.*—2.5 cm.
- *Quantity.*—15.
- *Diameter.*—3 mm.
- *Color.*—RHS Greyed-Orange 177A.
- *Aspect.*—Straight branches occurring on average 45° from center of plant.
- *Strength.*—Strong.

Internode length: Average 2 cm.

Stem pubescence: No.

FOLIAGE

Leaf:

- *Arrangement.*—Alternate, single.
- *Length.*—6 cm.
- *Width.*—3.75 cm.
- *Shape of blade.*—Broad elliptic.
- *Apex.*—Acute.
- *Base.*—Obtuse.
- *Margin.*—Crenate.
- *Texture of top surface.*—Leathery.
- *Texture of bottom surface.*—Rough, powdery, rigid veins.
- *Pubescence.*—None.
- *Color.*—Young foliage upper side: Near RHS Green 136B flushed Grey-Brown N199A, turning Green N137B. Young foliage under side: Near RHS Yellow-Green 148B, turning Greyed-Green 191B. Mature foliage late Summer upper side: Individual leaves have different colors. Some foliage solid RHS Red-Purple 59A, or Red 53C, or Yellow 9B. Some foliage Yellow 9B flushed Orange-Red 31A. Mature foliage late Summer under side: Individual leaves have different colors. Some foliage solid RHS Red-Purple 59A, or Red 53C, or Yellow 9B. Some foliage Yellow 9B flushed Orange-Red 31A. Fall foliage upper side: Individual leaves can have different colors, some near RHS Red 45A flushed Yellow-Orange 21A. Some foliage near Greyed-Purple 187A flushed 21A. Fall foliage under side: Glaucous. Near RHS Orange 24C.
- *Venation.*—Type: Pinnate. Venation color: Upper side: RHS Greyed-Green 160B. Under side: RHS Yellow-Green N144D.
- *Petiole.*—Length: 1 cm. Diameter: 1.5 mm. Texture: Upper side: Smooth, slightly glossy. Under side: Some pubescence. Color: Upper side: RHS Greyed-Purple 183A. Under side: RHS Greyed-Purple 183B.

FLOWER

Inflorescence and flower type and habit: Terminal spikes of brush like apetalous flowers having somewhat decorative filaments.

Quantity of flowers per inflorescence: 1.

Flower aspect: Upwards.

Quantity of flowers per lateral stem: 1.

Quantity of flowers per plant: Average 60.

Natural flowering season: Early Spring.

Shape: Bottle-brush.

Length: 3.5 cm.

Diameter: 2.5 cm.

Persistent or self-cleaning: Self-cleaning.

Fragrance: Moderate, pleasant earthy scent.

Bud:

- *Shape.*—Cylindrical.
- *Length.*—2 cm.
- *Diameter.*—13 mm.
- *Color.*—RHS Yellow-Green 144C.

Petals: None.

Sepals:

- *Quantity.*—5.
- *Appearance.*—Small.
- *Texture.*—Pubescent.
- *Arrangement.*—Whorl.
- *Shape.*—Elliptic.
- *Length.*—5 mm.
- *Width.*—3 mm.
- *Tip.*—Obtuse.
- *Base.*—Truncated.
- *Margin.*—Entire, pubescent.
- *Color.*—Upper side: RHS Yellow-Green 144C to Greyed-Orange 177A. Lower side: RHS Yellow-Green 144C to Greyed-Orange 177A.

Calyx:

- *Shape.*—Star-like.
- *Length.*—1 cm.
- *Diameter.*—1 cm.

Peduncle:
*Length.*—1.5 cm.
*Diameter.*—4 mm.
*Angle.*—45°.
*Strength.*—Strong.
*Texture.*—Pubescent.
*Color.*—RHS Greyed-Brown 199B.
Pedicels: None.

REPRODUCTIVE ORGANS

Stamens:
*Number.*—Approximately 100.
*Filament length.*—1.5 cm.
*Filament diameter.*—About 2 mm.
*Filament color.*—RHS White 155D.
*Anthers.*—Shape: Globular. Length: 1 mm. Color: RHS Greyed-Yellow 160C.
*Pollen.*—Amount: Moderate. Color: RHS Greyed-Yellow 160C.
Pistil:
*Number.*—One per flower.
*Length.*—3 mm.
*Style.*—Length: 2 cm. Color: RHS Yellow-Green 144B.
*Stigma.*—Shape: Globe. Color: RHS Yellow-Green 144B.

OTHER CHARACTERISTICS

Temperature tolerance: USDA Zones 5 though 8.
Disease/pest resistance: No unusual susceptibility to diseases or pests noted to date.
What is claimed is:
1. A new and distinct cultivar of *Fothergilla* plant named 'ALICE' as herein illustrated and described.

* * * * *